US00PP20314P2

(12) United States Plant Patent
Chaparro

(10) Patent No.: US PP20,314 P2
(45) Date of Patent: Sep. 15, 2009

(54) NECTARINE TREE NAMED 'UFROYAL'

(50) Latin Name: *Prunus persica*
Varietal Denomination: UFRoyal

(75) Inventor: Jose X. Chaparro, Gainesville, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/151,884

(22) Filed: May 9, 2008

(51) Int. Cl.
*A01H 5/00* (2006.01)

(52) U.S. Cl. ..... Plt./190

(58) Field of Classification Search ..... Plt./190
See application file for complete search history.

*Primary Examiner*—Annette H Para

(57) ABSTRACT

A new and distinct variety of nectarine tree, denominated 'UFRoyal', has a low winter chilling requirement estimated at 250 chill units (cu). The tree is medium size and moderately vigorous with a semi-spreading growth habit. It produces showy, pink flowers and small reniform leaf glands. Trees of 'UFRoyal' are self-fertile and regularly bear heavy annual crops of early season fruit that are large for its ripening season. Fruit are uniformly firm and yellow with non-melting flesh which are clingstone. Fruit are oval, and uniform with substantially symmetrical shape, and have an attractive 90 to 100% bright red skin. The fruit of 'UFRoyal' ripen about 1 week before 'UFQueen' nectarine in early May at Gainesville, Fla.

1 Drawing Sheet

Botanical classification: *Prunus persica.*—UFRoyal.

BACKGROUND OF THE NEW VARIETY

The present invention relates to a new and distinct variety of nectarine [*Prunus persica* (L.) Batsch] tree adapted to a subtropical (low chill) winter climate. This new tree, named 'UFRoyal', produces highly colored, good eating quality, clingstone, non-melting flesh fruit for fresh market in early May at Gainesville, Fla. Contrast is made to 'UFQueen' (U.S. Pat. No. 11,587) nectarine for reliable description. 'UFRoyal' is a promising candidate for commercial success in that it has large, attractive red skin, sweet fruit that ripen evenly within each fruit.

ORIGIN OF THE VARIETY

'UFRoyal' nectarine tree (genotype) originated in a cultivated area of a fruit breeding program located at Gainesville, Fla. where it was tested. It originated from an open-pollination of a cross of 'Fla. 86-28c' (unpatented) peach, of complex origin, hybridized with pollen of 'Suncoast' (unpatented) nectarine. 'UFRoyal' nectarine was selected in 1997 because it exhibited yellow, non-melting flesh, in early season with almost 100% red skin. It was designated and tested as 'Fla. 97-17cn'. It was asexually propagated in Gainesville, Fla. in 1997 by budding onto 'Flordaguard' (unpatented) seedling rootstock (for root-knot nematode control) and determined to have unique tree and fruit characteristics making it worthy for commercial fresh fruit production. There are no known effects of this standard rootstock on this scion cultivar. Asexually propagated plants remained true to the original tree and all characteristics of the tree and the fruit were transmitted.

SUMMARY OF THE VARIETY

The new and distinct variety of nectarine tree bears moderately early ripening fruit, and has a low chilling dormancy requirement. 'UFRoyal' blooms (showy flowers) in early February at Gainesville. The estimated chilling requirement is 250 chill units, based on bloom 3 to 5 days before 'UFQueen'. 'UFRoyal' nectarine tree is characterized by red skin fruit having firm, non-melting and yellow flesh. Fruit are clingstone and of good flavor and eating quality. The trees are vigorous, productive and regular bearing. Trees attain in two years, a height of two meters and a spread of one and a half meters (semi-spreading) at Gainesville. Terminal growth of up to a half meter annually is common on mature five-year-old trees with normal pruning to a vase shape.

The first fruit ripen in early May at Gainesville or in about 85 days from full bloom, which is about a week before 'UFQueen'. The fruit are uniformly medium large (about 120 to 140 g and equal to 'UFQueen'. Ripe fruit have near 100% solid (no stripes) red skin with a small amount of red pigment in the flesh, especially on trees stressed during hot, dry weather. There is no red pigment in the flesh at the pit. The flower anthers are light red, and leaf glands are reniform.

DESCRIPTION OF THE DRAWINGS

The accompanying drawing is a color photograph which shows a typical specimen of the fruit, leaf, and stem of the new variety as nearly true as it is reasonably possible to make in a color illustration of this type. The photograph shows an attractive shape and exterior coloration of four specimens of fruit above a ruler (side view, stem end view, blossom end view, and side view showing the suture), and a fruit cut longitudinally to show the pit.

DETAILED BOTANICAL DESCRIPTION

The tree, flowers, and fruit may vary in slight detail due to variations in soil type, cultural practices, and climatic condition. The potential for commercial production of fresh fruit by 'UFRoyal' is high, due to its attractive red skin over a bright yellow ground color, large fruit of good flavor, and good firmness with even ripening throughout the fruit. The present botanical description is that of the variety grown on 5-year-old trees on 'Flordaguard' rootstock under the ecological conditions prevailing at Gainesville, Fla. Colors (except those in common terms) are described from "The Pantone Book of Color", published by H. N. Abrams, Inc., N.Y. 1990.

Tree:

*Ploidy.*—Diploid.

*Size.*—Trees are medium stature when trained to an open vase form.

*Vigor.*—Moderately vigorous, and must be summer and winter pruned when grown to a vase shape to keep the tree open to get strong fruiting wood in the lower tree center. Trees respond typically to irrigation and fertilization. Tree growth of 4 to 6 feet in height and 3 to 5 feet in width occurs the first growing season in the field.

*Density.*—Light to medium in branching habit. Pruning is required to open the tree center to promote sunlight entrance for enhancing fruit color and sugar.

*Form.*—Semi-spreading and easily spread when pruned to vase shape.

*Hardiness.*—Hardy with respect to typical north central Florida winters.

*Bearer.*—Very productive annually without alternate bearing observed. Trees are self fertile and must be fruit thinned to avoid limb breakage and obtain large fruit size. Trees annually set several times the number of fruit for a desired crop load.

*Chilling requirement.*—Estimated endodormancy chilling requirement is 250 chill units based on time of bloom and leafing.

Trunk:

*Size.*—Medium trunk diameter attaining 8 cm diameter at a height of 30 cm at the end of 3 years growth at Gainesville.

*Texture.*—Medium smooth, but changes to medium shaggy as tree ages.

*Bark color.*—Older bark gray, Chinchilla (Pantone 17-1109).

*Lenticels.*—Moderate (12 to 16 per 4 square inches of surface area of trunk and medium (6 to 12 mm length perpendicular to the trunk) with the center being light brown, Medal Bronze (Pantone 17-0942).

Branches:

*Size.*—Strong growth of scaffold branches.

*Texture.*—Relatively smooth, numerous lenticels attaining size found on trunk and old scaffolds. Roughness increases with age.

*Color.*—New wood is light green Endive (Pantone 13-0632); Old wood is more brown, Clay (Pantone 15-1231).

*Crotch angles.*—Angles are selected at 45 to near 90 degrees in first year of tree training. Natural angles are within the normal range of standard varieties for a semi-spreading tree.

Leaves:

*Size.*—Medium; 15 to 18 cm length, including the petiole; 3 to 4 cm width. Measurements were made on vigorous upright shoots of summer growth.

*Thickness.*—Regular and no unusual variability detected.

*Form.*—Lanceolate.

*Apex.*—Acute.

*Margin.*—Serrulate, slightly undulate.

*Base.*—Cuneate.

*Surface.*—Upper, glabrous; Lower, medium large veins that are pinnately netted.

*Color.*—Lower surface is green, Mosstone (Pantone 17-0525); Upper surface is darker green, Avocado (Pantone 18-0430). Petiole and mid-vein show slight red anthocyanin in autumn, characteristic in peach and nectarine for 85 days or less in fruit development period (bloom to ripe).

*Glands.*—Two to 4, small reniform glands mostly on lower leaf blade, but occasionally on petiole. Leaf glands are moderately smaller than those on most commercial varieties. Leaf glands on young leaves are light green, Leek Green (Pantone 15-0628), darkening to Green Moss (Pantone 17-0636) on older leaves in mid-summer.

*Petiole.*—About 1 cm (0.9 to 1.2 cm) length; 1.3 mm diameter. Surface is light green, Lettuce Green (Pantone 13-0324). Grooved longitudinally.

*Stipules.*—Medium (equal to most commercial peach varieties), usually 2 per bud, and abscising just before leaf becomes full size in summer growth.

*Arrangement.*—Alternate.

Flower buds:

*Hardiness.*—Hardy with respect to north central Florida winters (16F minimum observed).

*Abundance.*—Very high due to shorter than average internode length. Most buds set fruit in absence of spring frosts and show little evidence of bud drop.

*Size.*—Medium, average 3.5 mm length in mid winter.

*Form.*—Plump, conic and free.

*Surface.*—Pubescent scales.

*Color.*—Brown, Stucco (Pantone 16-1412) in late summer.

Flowers:

*Blossom period.*—Three to 5 days before 'UFQueen' nectarine — average 50% bloom February 5 to 10 most years at Gainesville, but occurring over a 7–10 day period. Time and length of bloom are dependant on ambient temperature.

*Aroma.*—None detected.

*Flower density.*—Abundant, varying 1 to 3 per node, but usually 2. Density is high and about the same as that of 'UFQueen'.

*Type.*—Showy, location and seasonally variable within the range of commercial showy varieties. Average flower diameter, 40 mm. Average petal length, 18 mm; width, 11 mm. Texture is smooth.

*Color.*—Orchid Pink (Pantone 13-2010) at flower opening, and within the pink range of standard varieties.

*Flower parts.*—Stamens and pistil size, shape and color are within the range of standard commercial varieties. There are 5 sepals and petals. Sepals average 5 mm length and 4 mm wide near the base and are triangular shape with a dull point at the distal end. Sepals are red, Rapture Rose (Pantone 17-1929) on the exterior and green, Green Tea (Pantone 15-6428) on the interior, with a smooth pubescent margin. Sepals are pubescent and petals are glabrous. Pistils are usually 1 per flower. Pistil length (from tip of stigma to base of ovary) averages 21 mm. Pistils are light green, Pale Star (Pantone 12-0626). Flower pedicel is 1 to 2 mm length.

*Calyx cup.*—Medium small in the size range of commercial varieties. Cup diameter is 5 mm at the time of flower opening and internal color is orange, Tangerine (Pantone 15-1247).

*Stamen.*—Anthers are light red to yellow, Ginger (Pantone 17-1444), at flower opening, fading to yellow, Banana (Pantone13-0947), before pollen sheds, common to many nectarine varieties, regular size. Number of anthers varies from 24 to 35. Filaments are light green, Pale Star (Pantone 12-0626) and length is 9 to 13 mm.

*Pollen.*—Abundant and bright yellow, Snapdragon (Pantone 13-0840), common in many nectarine varieties.

*Fertility.*—Fully self fertile, and no cross pollination is required. Fruit set is abundant.

Fruit:

*Maturity when described.*—Tree ripe, May 5, 2006 at Gainesville.

*Date of picking.*—First, May 5, 2006; Last,— May 15, 2006 at Gainesville.

*Size.*—Uniform, medium large (large size for early mid-season maturity). Varies with fruit number per tee, soil type, climatic conditions and cultural practices. Average equatorial diameter.— 2¼ inches (58 mm). Average polar length (stem to distal end).— 2¼ inches (58 mm).

*Pedicel size and color.*—Length is approximately 7 mm; Width is approximately 3 mm. Color is Leek Green (Pantone 15-0628).

*Longitudinal section form.*—Slightly oval.

*Transverse section through diameter.*—Round.

*Suture.*—Shallow and inconspicuous.

*Ventral surface.*—Usually rounded.

*Base.*—Slightly cordate.

*Apex.*—Usually rounded to slightly obtuse.

*Crater at stem attachment.*—Flaring circular with fruiting branch depressing on base of fruit. Depth is 6 to 9 mm; breadth is 18 mm at top and 4 mm at pedicel attachment.

Skin:

*Thickness.*—Medium in comparison to commercial nectarine varieties.

*Texture.*—Medium in comparison to commercial nectarine varieties.

*Tenacity.*—Tenacious to flesh.

*Color.*—Red, Crimson (Pantone 19-1762), over 90 to 100% of skin. Ground color is bright yellow, Sunset Gold (Pantone 13-0940). Fruit exposed to sunlight have a higher degree of enhanced red skin.

*Tendency to crack.*—None observed.

*Taste.*—No astringency observed.

*Epidermis.*—Glabrous, waxy and smooth.

Flesh:

*Ripens.*—Evenly within each fruit.

*Texture.*—Firm, juicy, and non-melting when fully ripe.

*Fibers.*—Very fine, small, tender, and abundant.

*Aroma.*—Moderate and in the middle range of commercial nectarine varieties.

*Eating quality.*—Good, moderately sweet, slightly acid. Soluble solids were about 12 to 18 brix at 5.2 and 2.6 kg penetrometer (5/16 inch tip) firmness, respectively.

*Juice.*—Abundant.

*Color.*—Yellow, Apricot (Pantone 15-1153), with slight speckled red, Teaberry (Pantone 18-1756), in the flesh near the fruit tip, especially on stressed trees under dry, hot conditions. There is no red at the pit.

*Browning by oxidation.*—Very slight on tree ripe fruit beginning to soften.

*Amygdalin.*—Undetected.

Stone:

*Type.*—Clingstone.

*Size.*—Medium small: average length is 28 mm; average width is 23 mm; average thickness is 17 mm; average wall thickness is 5–6 mm.

*Color.*—Brown, Topaz (Pantone 16-1150) when freshly exposed.

*Form.*—Oblong.

*Base.*—Straight.

*Apex.*—Acute.

*Sides.*—Near equal.

*Surface.*—Irregularly furrowed toward the ventral edge, pitted from base to apex.

*Ridges.*—Jagged toward the base.

*Tendency to split.*—None observed.

*Seed.*—Bitter (amygdalin is abundant) kernel. Viable if stratified upon removal from fruit at harvest, and without drying. Kernel is brown, Sunflower (Pantone 16-1054) when first removed from ripe fruit. Side is 16 mm length, 11 mm wide and 4 mm thick. Shape is acute tip with obtuse base and overall ovate shape.

Use: Fresh; dessert.

Resistance to disease: High resistance to bacterial spot incited by *Xanthomonas campestris* pv. *pruni* (Pers.) Diet. Resistance to other fruit and tree diseases are within the range for commercial nectarine cultivars in Florida. No unusual resistance or susceptibility to insects and diseases noted.

Keeping quality: Excellent after 14 days at 2C and with minimal bruises or scarring appear on skin.

Shipping quality: Degree of firmness at harvest and firmness retained in refrigeration for 14 days at 2C, with no internal breakdown of flesh or appreciable loss of eating quality, indicates fruit should be highly acceptable for shipping.

We claim:

1. A new and distinct nectarine tree variety as illustrated and described, characterized by a low chilling requirement, and bearing fruit having firm, yellow and non-melting, clingstone flesh of high eating quality and an attractive, high percentage red skin with fruit ripening in early May or about 1 week before 'UFQueen' at Gainesville, Fla.

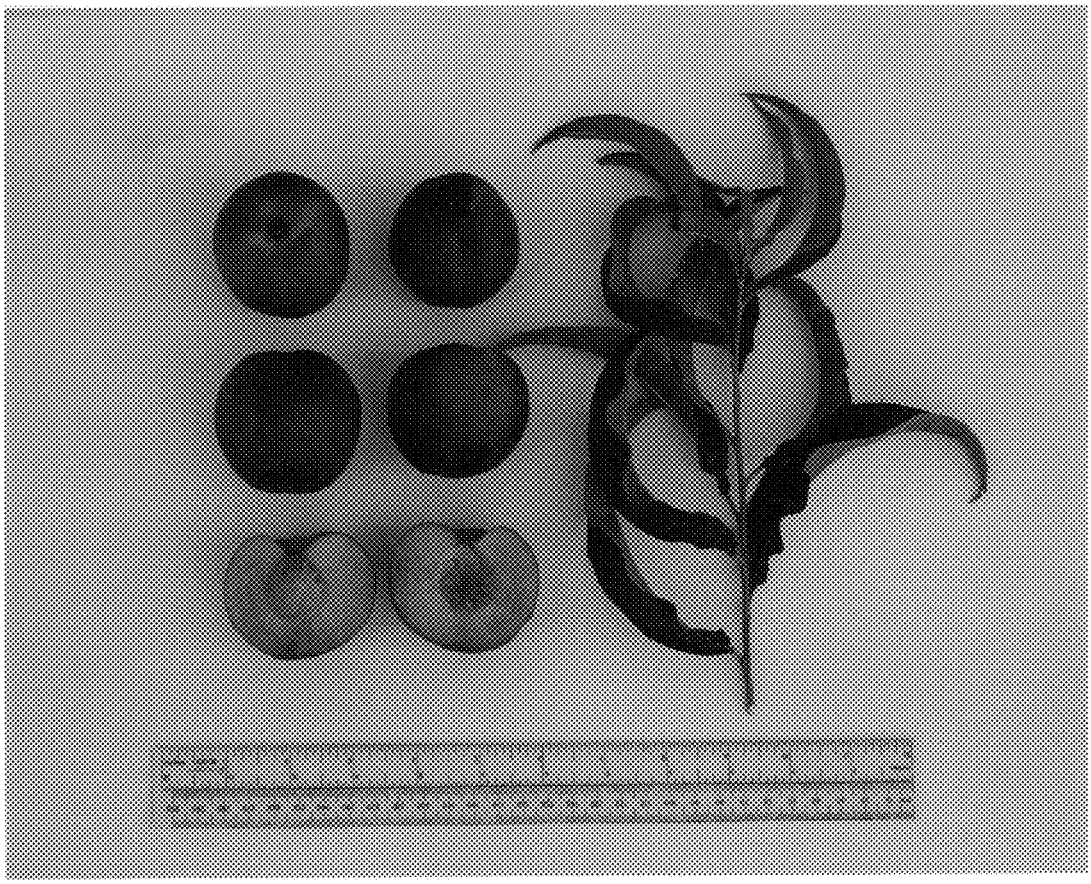

* * * * *